US00PP10009P

United States Patent [19]

Svejda et al.

[11] Patent Number: Plant 10,009

[45] Date of Patent: Aug. 26, 1997

[54] SHRUB ROSE PLANT NAMED 'GEORGE VANCOUVER'

[75] Inventors: Felicitas J. Svejda, Nepean; Ian S. Ogilvie, Pointe Claire, both of Canada

[73] Assignee: Her Majesty the Queen in right of Canada, as represented by the Minister of Agriculture, Ottawa, Canada

[21] Appl. No.: 665,101

[22] Filed: Jun. 10, 1996

[51] Int. Cl.[6] ..... A01H 5/00

[52] U.S. Cl. ..... Plt./1

[58] Field of Search ..... Plt./1, 22, 28, Plt./27

[56] References Cited

PUBLICATIONS

Ogilvie, Ian S. and Neville P. Arnold, "'George Vancouver' Rose." *Hort Science* 30(1):146 (Feb. 1995).

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms in clusters attractive medium red blossoms that tend to lighten somewhat when fully open. The new variety exhibits an upright growth habit with glossy foliage, and good winter hardiness. Resistance to powdery mildew and blackspot has been observed. The new variety propagates well by the use of softwood stem cuttings, and is well adapted for growing as colorful ornamentation in the landscape.

2 Drawing Sheets

SUMMARY OF THE INVENTION

The new variety of shrub rose plant of the present invention was created by artificial pollination at the Central Experimental Farm, Ottawa, Ontario, Canada. The female parent (i.e., the seed parent) was the L83 line (non-patented in the United States) and the male parent (i.e., the pollen parent) was the E10 line (non-patented in the United States). The L83 line was derived from a cross between *Rosa kordesii* and breeding line G49 which originated as a selection from line G12×*Rosa kordesii*. *Rosa kordesii* originated from a spontaneous tetraploid from 'Max Graf' (non-patented in the United States), a hybrid between the diploid species *Rosa wichuriana* Crepin and *Rosa rugosa*, Thunberg, one of the hardiest rose species known. The E10 line originated from a cross between the L15 line (non-patented in the United States) and 'Champlain' (non-patented in the United States). Line L15 had a complex pedigree and was derived from *Rosa kordesii* and breeding line D07 (non-patented in the United States). Line D07 resulted from the open pollination of seedlings derived from a cross between 'Red Dawn' (non-patented in the United States) and 'Suzanne' (non-patented in the United States). The breeding program was designed to impart a high degree of winter hardiness to the offspring.

It was found that the new variety of shrub rose plant of the present invention possesses the following combination of characteristics:

(a) exhibits an upright growth habit with attractive dark green glossy foliage,
(b) forms in clusters attractive medium red blossoms that tend to lighten when fully open,
(c) propagates well by the use of softwood cuttings,
(d) exhibits a good winter hardiness, and
(e) is particularly well suited for growing as ornamentation in the landscape.

The rose plant can be grown well on its own roots out-of-doors without protection at L'Assomption, Quebec, Canada. The blossoms commonly appear in large quantities during June and repeat throughout the summer to late September. Resistance to powdery mildew and blackspot has been exhibited.

While the new variety resembles 'Champlain' (non-patented in the United States) somewhat with respect to blossom color and foliage, it can be readily distinguished by greater hardiness, greater fertility, and greater resistance to mildew.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings conducted at L'Assomption, Quebec, Canada.

The new variety has been named 'George Vancouver'.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed while growing on their own roots at L'Assomption, Quebec, Canada.

DETAILED DESCRIPTION

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—A five year-old plant commonly assumes a height of approximately 0.9 m.

*Width.*—A five year-old plant commonly assumes a width of approximately 1 m.

*Habit.*—Upright.

Thorns:

*Quantity.*—Approximately 16±3 thorns per 100 mm. of stem on average.

Leaves: Compound and pinnate.

*Leaflets.*—Number: commonly 5 or 7. Frequency: abundant. Shape: ovate and acuminate. Margins: dentate. p'*Color.*—Adult foliage: dark green, Yellow-Green Group 147A on upper surface and Yellow-Green Group 147B on under surface. Texture: leathery. General appearance: dark green, and glossy.

Inflorescence:

*Number of flowers.*—Commonly in clusters of 1 to 6.

Figure 1:
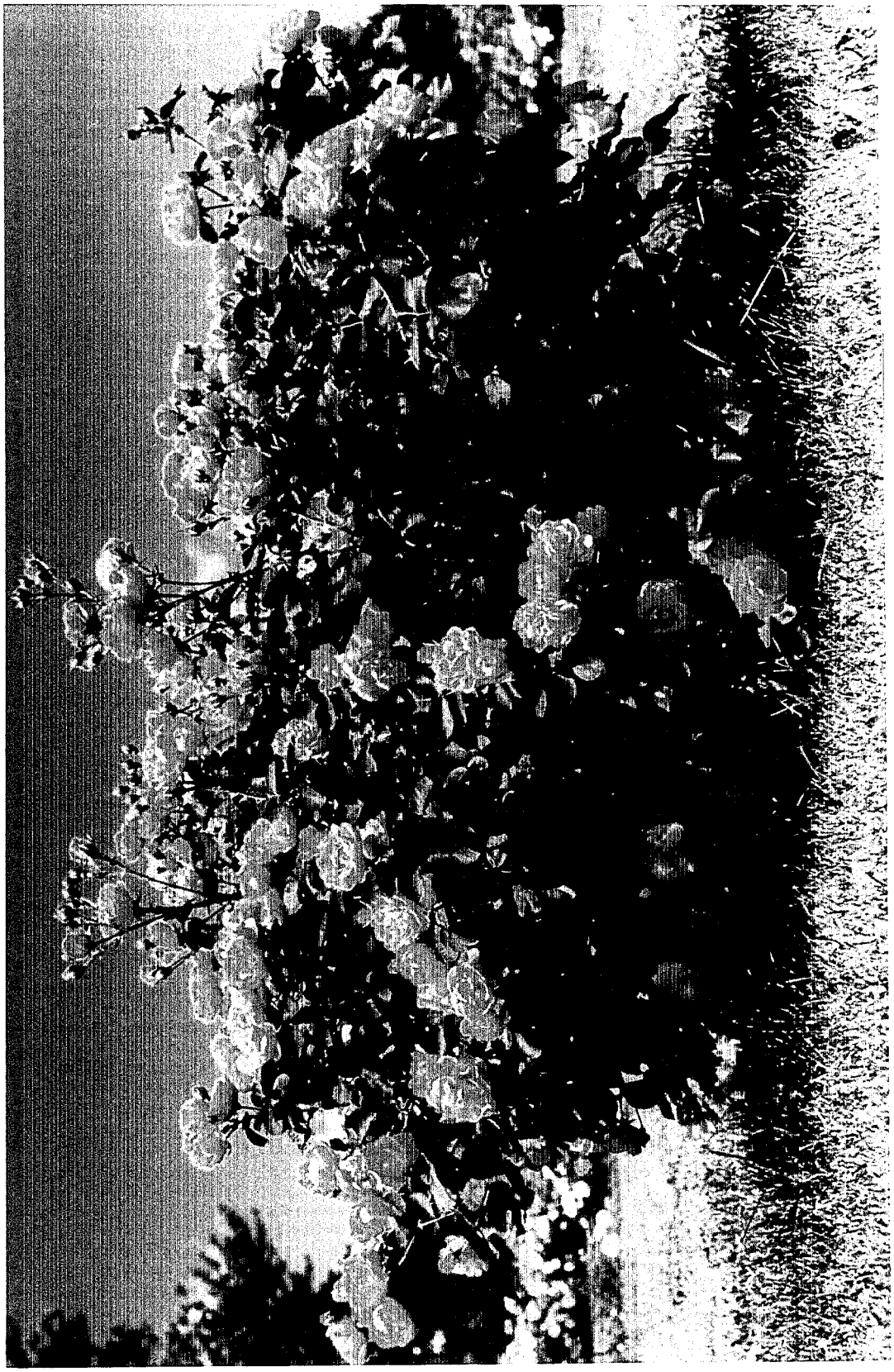
FIG. 1 illustrates a typical flowering plant of the new variety while growing in the landscape. The upright growth habit, abundant foliage, and profusion of blossoms are apparent.
Figure 2:
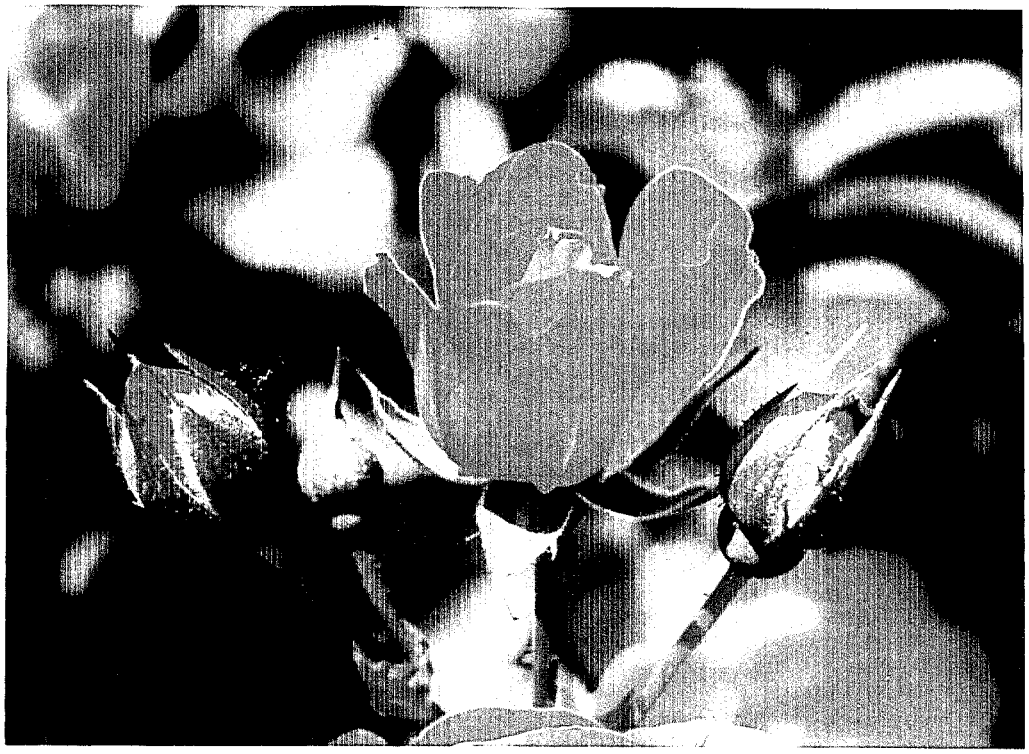
FIG. 2 illustrates typical blossoms and buds in various stages of opening of the new variety.

*Peduncle.*—Erect, and reddish as shown in FIG. 2.

*Sepals.*—Configuration: broad with some extensions as shown in FIG. 2.

*Buds.*—Shape: ovoid before the opening of the sepals, as shown in FIG. 2. Color upon opening: the outer petals are deep red as illustrated in FIG. 2.

*Flower.*—Shape: initially cup-shaped and subsequently assumes a more flattened configuration (as illustrated). Diameter: approximately 60 mm. on average. Color (when blooming): medium red, Red-Purple Group 57B on the upper surface and Red-Purple Group 57D on the under surface. The coloration of the blossoms commonly fades to a lighter pink when the blossoms are fully mature. Fragrance: slight. Petal number: approximately 24±4 on average. Petal drop: petals tend to detach fairly clearly. Fertility: flowers are fertile and under open pollination most flowers unless removed form hips that commonly exhibit an attractive red appearance. Lasting quality: the blossoms commonly last 3 to 5 days when cut and placed in a vase and generally last longer on the plant. The blossom life is influenced by temperature and other environmental conditions that are encountered.

Development:

*Vegetation.*—Good vigor.

*Blossoming.*—In large quantities during June with repetition throughout the summer to late September.

*Hardiness.*—Has survived test winters to −35° C. without protection except for natural snow with only slight winter injury.

*Resistance to diseases.*—A high resistance to powdery mildew [*Sphaerotheca pannosa* (Wallr. ex Fr.) Lev.] and blackspot (*Diplocarpon rosae* Wolf.) has been observed.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20° to 25° C. ambient temperature.

We claim:

1. A new and distinct variety of shrub rose plant characterized by the following combination of characteristics:

(a) exhibits an upright growth habit with attractive dark green glossy foliage,
(b) forms in clusters attractive medium-red blossoms that tend to lighten when fully open,
(c) propagates well by the use of softwood cuttings,
(d) exhibits a good winter hardiness, and
(e) is particularly well suited for growing as ornamentation in the landscape;

substantially as herein shown and described.

* * * * *